United States Patent
Pizza

(10) Patent No.: US 10,342,813 B2
(45) Date of Patent: *Jul. 9, 2019

(54) CALCIUM GLUCONATE SOLUTIONS IN FLEXIBLE CONTAINERS

(71) Applicant: HQ SPECIALTY PHARMA CORPORATION, Paramus, NJ (US)

(72) Inventor: Joseph Pizza, Palm Beach, FL (US)

(73) Assignee: HQ SPECIALTY PHARMA CORPORATION, Paramus, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/188,808

(22) Filed: Nov. 13, 2018

(65) Prior Publication Data

US 2019/0076454 A1 Mar. 14, 2019

Related U.S. Application Data

(63) Continuation of application No. 15/868,705, filed on Jan. 11, 2018, now Pat. No. 10,130,646, which is a continuation of application No. 15/659,184, filed on Jul. 25, 2017, now abandoned.

(51) Int. Cl.
*A61K 31/702* (2006.01)
*C07C 59/105* (2006.01)
*A61K 31/7012* (2006.01)

(52) U.S. Cl.
CPC ........ *A61K 31/7012* (2013.01); *C07C 59/105* (2013.01); *A61K 31/702* (2013.01)

(58) Field of Classification Search
CPC .................................................. A61K 31/702
USPC .......................................................... 514/554
See application file for complete search history.

(56) References Cited

U.S. PATENT DOCUMENTS

| 1,965,535 | A | 7/1934 | Pasternack |
| 8,829,054 | B1 | 9/2014 | Owoo |
| 10,130,646 | B1 * | 11/2018 | Pizza .................... C07C 59/105 |

OTHER PUBLICATIONS

Allen Loyd V Jr., "Tonicity-Adjusting Agents, Features Excipient:", International Journal of Pharmaceutical Compounding, May/Jun. 2000.

* cited by examiner

*Primary Examiner* — Kevin E Weddington
(74) *Attorney, Agent, or Firm* — Oblon, McClelland, Maier & Neustadt L.L.P.

(57) ABSTRACT

A terminally sterilized aqueous calcium gluconate solution comprising 1 to 15 wt. % calcium gluconate and from 1 to 19 wt. parts of calcium saccharate per 100 wt. parts of calcium gluconate packaged in a flexible plastic container with the remainder water.

5 Claims, No Drawings

CALCIUM GLUCONATE SOLUTIONS IN FLEXIBLE CONTAINERS

CROSS REFERENCE TO RELATED APPLICATIONS

This application is a Continuation of U.S. Ser. No. 15/868,705 filed Jan. 11, 2018, allowed, which is a continuation of U.S. Ser. No. 15/659,184 filed Jul. 25, 2017, abandoned, the entire contents of which are incorporated herein by reference.

FIELD OF THE INVENTION

The invention relates to aqueous calcium gluconate solutions in flexible plastic bags. The solution in the bag is terminally sterilized.

BACKGROUND OF THE INVENTION

Calcium gluconate is used for treating individuals having low levels of calcium ions in their blood system. Often the calcium gluconate is administered orally. However, in more serious calcium deficiency conditions, it is necessary to rapidly increase the amount of calcium ions in the person's blood system which requires administration of calcium via intravenous means. When the individual with the hypocalcemia is a child, in a pediatric intensive care unit, it is almost by necessity that the calcium gluconate is administered intravenously. In severe cases, there could be life threatening complications including cardiac arrhythmias.

Calcium gluconate is an old drug dating back to at least the 1930s, and is available as aqueous solutions of calcium gluconate in 10 mL glass vials and 100 mL rigid plastic bottles. Calcium gluconate is sold as a supersaturated solution which must be administered at a slow rate. The glass vials have a number of disadvantages. First, is the possibility of breakage with the scattering of glass particles. Second, for glass vials and plastic bottles it is necessary to often dilute the calcium gluconate solution in an IV bag so as to allow intravenous (IV) administration at the appropriate rate. Finally, both the glass and rigid plastic containers take up more storage space than the flexible plastic bag products used for IV administration of drugs and other solutions.

Mixtures of calcium gluconate with calcium saccharate are described in U.S. Pat. No. 1,965,535. This patent teaches preparing calcium gluconate solutions containing calcium saccharate as a stabilizer which can be stored in glass containers after suitable sterilization or the use of a preservative agent. The patent cautions that the solution must be protected from "infection" since fermentation readily occurs in the presence of microorganisms.

Hospitals avoid the use of glass and rigid plastic vials and bottles in patient rooms and either will directly transfer the calcium gluconate from the container into plastic bags, which are then used for IV administration or have such bags prepared in advance by adding the calcium gluconate solution to an IV solution. Such pre-prepared bags may be done at the hospital or by a compounder. However the bags so prepared have a limited shelf life at room temperature, typically on the order of about 45 to 70 days. Unused product cannot be used after the expiration date and must be properly disposed of. As a result, hospitals cannot maintain a significant inventory of the calcium gluconate in the plastic IV bags but must often replenish their supply.

In contrast, the calcium gluconate solutions sold in glass and rigid plastic vials are reported to have shelf lives of about three years. Thus, there exists a need for a calcium gluconate aqueous solution product in plastic bags which has a long shelf life.

SUMMARY OF THE INVENTION

This invention relates to aqueous calcium gluconate solutions which have long-term storage stability when stored in a flexible plastic container. The calcium gluconate solution in the flexible plastic container is subjected to terminal sterilization via moist-heat autoclaving so that the product is in a sterile condition. The product in the bag can be administered to the patient using conventional IV technology. The calcium gluconate solution will conventionally contain, in addition to the calcium gluconate, calcium saccharate as a stabilizer.

DETAILED DESCRIPTION OF THE PREFERRED EMBODIMENTS

Calcium gluconate aqueous solutions are most commonly available as super saturated solutions containing about 15 mg/mL-25 mg/mL calcium gluconate, 0.6 mg/mL-1.5 mg/mL calcium saccharate, sufficient sodium chloride to provide an isotonic solution. A more preferred solution comprises 19.6 mg/ml of calcium gluconate monohydrate, about 0.9 mg/ml of calcium D-saccharate, about 6.75 mg/ml sodium chloride to adjust tonicity and hydrochloric acid or sodium hydroxide to adjust the pH as needed. The pH will often be adjusted to about 7-8, the psychological pH but a higher or lower pH is possible. Normally the pH will be between 5 and 8.5, more preferably between 6.0 and 8.2, and most preferably between 7 and 8. The sodium chloride may be replaced in whole or in part by a sufficient quantity of calcium chloride or potassium chloride or a mixture of both in an amount sufficient to provide an isotonic solution. A solution is considered to be isotonic if it has an osmolality of between about 260 and 320 mosm/kg. The use of sugars such as dextrose should be avoided as they may impact the stability of the solution to terminal sterilization and adversely impact the storage life of the solution. The calcium saccharate is added to stabilize the supersaturated calcium gluconate solution. The calcium D-saccharate has been found to be particularly suitable for this purpose. Other calcium saccharates may be used provided the resulting supersaturated solution is stable. The suitability of other calcium saccharates can be determined using the procedure described in U.S. Pat. No. 1,965,535 which incorporated herein by reference. Solutions having lower calcium gluconate concentrations are also included.

The calcium gluconate concentration in the formulation is not limited. Concentrations of from 1 to about 15 wt. % are preferred, still more preferred are concentrations of about 6 to 12 wt. %, with the most preferred being about 10 wt. %. The amount of calcium gluconate in the solution is limited by the calcium gluconate's solubility in the aqueous medium. Solutions of from 1 to 10% calcium gluconate require about 1 to 19 parts of calcium saccharate per 100 parts of calcium gluconate. For a 10% calcium gluconate solution, the amount of calcium saccharate is from about 2 parts to 5 parts per 100 hundred parts of calcium gluconate. All parts are by weight. The maximum calcium saccharate solubility in calcium gluconate solution is about 19 parts per 100 parts calcium gluconate.

The amount of the tonicity adjusting agent added is usually an amount sufficient to make the solution isotonic. The tonicity adjusting agent may be omitted if an isotonic solution is not required. While sodium chloride is a common tonicity adjusting agent, any of the conventional tonicity adjusting agents may be used provided the agent does not adversely impact the stability of the solution.

The preferred composition comprises 19.6 mg/ml of calcium gluconate monohydrate, about 0.9 mg/ml of calcium D-saccharate, and about 6.75 mg/ml sodium chloride to adjust tonicity and hydrochloric acid or sodium hydroxide to adjust the pH as needed. Other physiologically accepted acids and bases may be used to adjust the pH of the solution. Normally the pH is adjusted from 5.5 to about 8.5, preferably from about 6 to 8.2.

Calcium gluconate solutions are compatible with the following intravenous solutions and drugs: sodium chloride for injection 0.9%, lactated Ringer's injection, dextrose 5%-20%, dextrose-lactated Ringer's injection, dextrose-saline combinations, amikacin sulfate, aminophylline, ascorbic acid injection, bretylium tosylate, cephapirin sodium, chloramphenicol sodium succinate, corticotropin, dimenhydrinate, erythromycin gluceptate, heparin sodium, hydrocortisone sodium succinate, lidocaine HCl, methicillin sodium, norepinephrine bitartrate, penicillin G potassium/sodium, phenobarbital sodium, potassium chloride, tobramycin sulfate, vancomycin HCl, verapamil and vitamin B-complex with C.

The calcium gluconate solutions of the invention should be free of agents which will cause the calcium gluconate to precipitate from solution. Materials which may impact the calcium gluconate solutions include phosphate salts, oxytetracycline HCl, prochlorperazine edisylate, and tetracycline HCl. Compatibility is dependent upon factors such as pH, concentration, temperature and diluents used. If these materials are to be included the solution, the stability of the calcium gluconate solution should be investigated.

Calcium gluconate is reportedly incompatible with the following solutions or drugs: intravenous fat emulsion, amphotericin B, cefamandole naftate, cephalothin sodium, dobutamine HCl, methylprednisolone sodium succinate, and metoclopramide HCl.

The flexible plastic container must be one which is compatible with calcium gluconate. It must also be able to undergo heat sterilization in moist steam without contaminating the calcium gluconate solution. Suitable flexible plastic containers are those made of copolymerized ethylene and vinyl acetate. Preferably the bag is laminated with the inner most layer comprising copolymerized ethylene and vinyl acetate. More preferably the bag comprises from 3 to 7 layers. These materials are commercially available under the tradename Nexcel® by Sealed Air. The volume of the bag is dependent on the volume of premixed formula. The volume of premixed formula can be from 10 ml to 1000 ml, preferable 50 ml and 100 ml based on current calcium gluconate dosing. Larger or smaller volumes can be used depending on dosing requirements. CR3 elastomer copolyester ether bags may also be used for formulations to be sterilized in moist steam provided but are not preferred.

In an embodiment of the present invention, provided are a flexible plastic container with modified ports and closure system suitable for storing Calcium gluconate formulations of the present invention which is subjected to typically product sterilization by steam sterilization (e.g., autoclaving, 121° C. for about 20 minutes) without altering the thermal properties of the film layers, ports and closure system as well as maintaining the integrity container. The primary polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer etc. In addition to plastic bags, CZ resin containers, polypropylene and similar resins can be used as rigid containers and syringes.

The ports and the closure system preferably uses commerciality available polymers, elastomers etc. In an exemplary embodiment of the present invention, the administrative and additive ports can be made off external coextruded layer consists of synthetic thermoplastic rubber (Raumedic SRT320) ranging from about 20 to 30% based on an elastomer modified polypropylene. While the internal coextruded layer (PE770) of not more that 50% in composition consists of ethylene vinyl acetate without any further additives (EVA). The tubing ports can be made of two-layer materials, which can withstand both terminal sterilization and co-solvent matrix. Furthermore, the twist-off compositions can be made of polyproplene Granuflex® 4489 between 70-80% and Granuflex®4371 15-20%. Alternatively the port tube may be a bilayer tube comprising an outer layer of polypropylene and an inner layer of EVA and the twist off made of LDPE and PP. However, other polymers stable, low leachables, and without physical deformation during heat sterilization may also be used for the ports and closure assemblies.

Commercially available flexible plastic containers (bags) such as Excel® (Braun Company) comprising a three-layered ethylene-polypropylene bag having polyester elastomer outer layer, Visiv® (Hospira), Nexcel® (Sealed Air), Intervia® (Baxter) preferably with a non-DEHP fluid path, Technoflex polyolefin bags, etc., for pharmaceutical formulation or medical liquids are assembled of different plastic materials of different properties, thermal resistance and functionalities. They are typically designed and tested mostly for aqueous formulations admixtures, premixed or ready-to-use pharmaceutical products. Still the combination of the co-solvents and drug composition subjected to further heat sterilization can adversely effect, plastic materials, sealing integrity and the solutions contained therein unless they are maintained at certain conditions. Thus, the plastic container should be checked after sterilization for integrity before using it for the formulation. In addition, the formulation after sterilization should be analyzed for the presence of substances leached from the container as a result of the sterilization cycle.

In another alternative embodiment, provided are a flexible plastic container with modified ports and closure system suitable for storing calcium gluconate formulations of the present invention which is subjected to typically product sterilization by steam sterilization (e.g., autoclaving, 121° C. for about 15 to 20 minutes) without altering the thermal properties of the film layers, ports and closure system as well as maintaining the integrity container. The primary polymeric materials which may be used include: polysulfone, polycarbonate, polypropylene, polyethylene (LDPE or HDPE), ethylene/propylene copolymers, polyolefins, acrylic-imide copolymers, polyester (e.g. PET, PEN and the like), Teflon, Nylon, acetal (Delrin), polymethylpentene, PVDC, ethylvinylacetate, AN-copolymer etc.

Sterilization is accomplished by heat sterilization. Heat sterilization is normally performed using steam, preferably wet steam to allow for the use of pressure as a means of temperature control. The time period for the sterilization must be long enough to meet the sterility requirements required of an injectable product. When steam is used the period may be from about 5 to 30 minutes at temperatures of about 110° C. to 130° C., or from about 10 to 30 minutes at temperatures of about 110° C. to 130° C., preferably at 120° C. to 125° C. for 15 to 30 minutes. In another embodiment, the sterilization can be at 120° C. for 5 to 20 minutes.

Having generally described this invention, a further understanding can be obtained by reference to certain specific examples, which are provided herein for purposes of illustration only, and are not intended to be limiting unless otherwise specified.

In the examples which follow, the compositions were made as follows:

The formulation was packaged in 100 mL bags. One portion was used to fill the 100 mL Nexcel M312A Bag 1P with 50 mL of the calcium gluconate solution and the second was used to fill the same Nexcel bags with 100 mL of the solution. The bags were then terminally sterilized in a steam autoclave at 121° C. for 20 minutes. After sterilization the bags were subjected accelerated stability testing at 40° C.±2° C./15% RH±5% RH. In example 1 the results for the bags with the 50 mL solution are reported and in Example 2 the results for the 100 mL solution are reported.

EXAMPLE 1

50 mL Bag Containing 1 Gram Calcium Gluconate

| Test (U.M.) | Shelf life | 0 | 1 | 2 | 3 | 6 |
|---|---|---|---|---|---|---|
| Clear, Colorless solution (—) | Complies | Complies | Complies | Complies | Complies | Complies |
| Free from visible particles (—) | Complies | Complies | Complies | Complies | Complies | Complies |
| pH (pH Units) | 6.0-8.2 | 6.6 | 6.3 | 6.2 | 6.3 | 6.3 |
| Osmolality (mOSmo/Kg) | 270-320 | 298 | 304 | 297 | 306 | 311 |
| Assay Calcium (% Labelled Claim) | 95.0-105.0 | 101.1 | 101.2 | 101.1 | 101.6 | 101.3 |
| Assay Chloride (mmol/L) | 109.7-121.3 | 116.1 | 116.0 | 116.4 | 117.2 | 116.9 |
| Extractable Volume (ml) | >=50 | 53.7 | 53.7 | 53.7 | 53.7 | 53.7 |
| Weight Loss (%) | <=2.0 | 0.0 | 0.0 | 0.0 | 0.0 | 0.0 |
| Particles >= 10 micron (N. Part/Bag) | <=6000 | 0 | 100 | 50 | 50 | 0 |
| Particles >= 25 micron (N. Part/Bag) | <=600 | 0 | 0 | 0 | 0 | 0 |
| Bacterial Endotoxins (EU/mg) | <0.17 | <0.08475 | — | — | — | <0.08475 |
| Sterility (Parametric Release per SOP GEN094) (—) | Comply | Comply | — | — | — | — |
| Sterility (Container Integrity) (—) | Comply | — | — | — | — | Comply |

EXAMPLE 2

100 mL Bag Containing 2 Grams of Calcium Gluconate

| Test (U.M.) | Shel life | 0 | 1 | 2 | 3 | 6 |
|---|---|---|---|---|---|---|
| Clear, Colorless solution (—) | Complies | Complies | Complies | Complies | Complies | Complies |
| Free from visible particles (—) | Complies | Complies | Complies | Complies | Complies | Complies |
| pH (pH Units) | 6.0-8.2 | 6.7 | 6.3 | 6.3 | 6.3 | 6.4 |
| Osmolality (mOSmo/Kg) | 270-320 | 301 | 297 | 301 | 302 | 307 |
| Assay Calcium (% Labelled Claim) | 95.0-105.0 | 99.8 | 99.7 | 99.6 | 99.9 | 99.4 |
| Assay Chloride (mmol/L) | 109.7-121.3 | 114.5 | 114.9 | 114.6 | 115.2 | 114.9 |
| Extractable Volume (ml) | >=100 | 104.0 | 104.0 | 104.0 | 104.0 | 104.0 |
| Weight Loss (%) | <=2.0 | 0.0 | 0.0 | 0.0 | 0.0 | 0.0 |
| Particles >= 10 micron (N. Part/Bag) | <=6000 | 200 | 200 | 100 | 100 | 0 |
| Particles >= 25 micron (N. Part/Bag) | <=600 | 0 | 0 | 0 | 0 | 0 |
| Bacterial Endotoxins (EU/mg) | <0.17 | <0.08475 | — | — | — | <0.08475 |
| Sterility (Parametric Release per SOP GEN094) (—) | Comply | Comply | — | — | — | — |
| Sterility (Container Integrity) (—) | Comply | — | — | — | — | Comply |

As can be seen from the results, the calcium gluconate solution was virtually unchanged after six months of accelerated stability testing in both examples. This test is equivalent of 24 months at 25° C.+/−2° C. and 40%±5% relative humidity. These results are surprising in view of the prior art disclosures of only a short shelf life for the prior art calcium gluconate bag formulations.

Obviously, numerous modifications and variations of the present invention are possible in light of the above teachings. It is therefore to be understood that within the scope of the appended claims, the invention may be practiced otherwise than as specifically described herein.

The invention claimed is:

1. A terminally sterilized aqueous calcium gluconate solution comprising 1 to 15 wt. % calcium gluconate and from 1 to 19 wt. parts of calcium saccharate per 100 wt. parts of calcium gluconate packaged in a flexible plastic container with the remainder water,
   wherein the solution has a pH of from 6.0 to 8.2.

2. The terminally sterilized aqueous calcium gluconate solution of claim 1 wherein the flexible container is a bag.

3. The terminally sterilized aqueous calcium gluconate solution of claim 2 further comprising a tonicity agent.

4. The terminally sterilized aqueous calcium gluconate solution of claim 1 wherein the solution has a pH of from 6.0 to 6.7.

5. The terminally sterilized aqueous calcium gluconate solution of claim 1 wherein the solution has a pH of from 6.2 to 6.7.

* * * * *